United States Patent
Zhao et al.

(10) Patent No.: US 9,194,811 B1
(45) Date of Patent: Nov. 24, 2015

(54) APPARATUS AND METHODS FOR IMPROVING DEFECT DETECTION SENSITIVITY

(71) Applicant: KLA-Tencor Corporation, Milpitas, CA (US)

(72) Inventors: Guoheng Zhao, Palo Alto, CA (US); Sheng Liu, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 27 days.

(21) Appl. No.: 14/231,412

(22) Filed: Mar. 31, 2014

Related U.S. Application Data

(60) Provisional application No. 61/806,994, filed on Apr. 1, 2013.

(51) Int. Cl.
 *G01N 21/00* (2006.01)
 *G01N 21/88* (2006.01)

(52) U.S. Cl.
 CPC .................................. *G01N 21/8806* (2013.01)

(58) Field of Classification Search
 CPC .... G02B 21/06; G02B 21/361; G02B 21/002; G02B 21/367; G02B 27/095; G02B 27/58; G02B 21/0004; G02B 21/0096; G02B 21/14; G02B 21/16; G02B 21/36; G02B 21/365; G02B 21/0032; G02B 21/0076
 See application file for complete search history.

(56) References Cited

U.S. PATENT DOCUMENTS

| | | | |
|---|---|---|---|
| 5,916,711 A * | 6/1999 | Salik et al. | 430/5 |
| 6,191,850 B1 * | 2/2001 | Chiang | 356/237.4 |
| 7,221,444 B1 | 5/2007 | Zhao | |
| 8,614,790 B2 | 12/2013 | Berlatzky et al. | |
| 2001/0030744 A1 | 10/2001 | Chang | |
| 2008/0304058 A1 | 12/2008 | Heiden | |
| 2010/0149551 A1 | 6/2010 | Malinkevich | |
| 2013/0016346 A1 | 1/2013 | Romanovsky et al. | |

(Continued)

FOREIGN PATENT DOCUMENTS

WO 2011161024 A1 12/2011

OTHER PUBLICATIONS

Chowdhury, Shwetadwip, et al., "Structured Oblique Illumination Microscopy for Enhanced Resolution Imaging of Non-Fluorescent, Coherently Scattering Samples", Biomedical Optics Express, vol. 3, No. 8, Aug. 2012, pp. 1841-1854.

(Continued)

*Primary Examiner* — Michael P Stafira
(74) *Attorney, Agent, or Firm* — Kwan & Olynick LLP

(57) ABSTRACT

Disclosed are methods and apparatus for detecting defects in a semiconductor sample. The system includes an illumination optics module for simultaneously scanning two or more structured illumination (SI) patterns across the sample in a scan direction. The SI patterns have a phase shift with respect to each other, and the SI patterns are parallel to the scan direction. The system also includes a collection optics module for collecting output light from the sample in response to the SI patterns that are scanned across the sample and two or more detectors for individually detecting the output light collected for individual ones of the SI patterns. The system includes a controller to generate two or more SI images for the SI patterns based on the individually detected output light and detect defects on the sample by performing a comparison type inspection process based on the two or more SI images.

21 Claims, 11 Drawing Sheets

(56) References Cited

U.S. PATENT DOCUMENTS

2013/0100525 A1* 4/2013 Chiang et al. ............... 359/385
2013/0229665 A1* 9/2013 Nomura ....................... 356/601
2013/0342886 A1* 12/2013 Cooper ...................... 359/204.3

OTHER PUBLICATIONS

Kudo, R., et al., "Fundamental Verification for 2-Dimensional Super-Resolution Optical Inspection for Semiconductor Defects by Using Standing Wave Illumination Shift", XIX IMEKO World Congress, Fundamental and Applied Metrology, Sep. 6-11, 2009, pp. 106-111.

Usuki, Shin, "Advanced Microscopic Imaging by Spatial Control of Light and Multi-Image Reconstruction", ISUPEN, 2012, pp. 1-6.

Usuki, Shin, et al., "Resolving Power Improvement for Optical Nano-Defect Measurement by Using Sub-Pixel Sampling based on Structured Illlumination Shift Method", Asian Symposium for Precision Engineering and Nanotechnology, 2009, 5 pgs.

* cited by examiner

APPARATUS AND METHODS FOR IMPROVING DEFECT DETECTION SENSITIVITY

CROSS-REFERENCE TO RELATED APPLICATION

This application claims priority to U.S. Provisional Patent Application No. 61/806,994, filed 1 Apr. 2013, which application is incorporated herein by reference in its entirety for all purposes.

TECHNICAL FIELD OF THE INVENTION

The invention generally relates to the field of wafer and reticle inspection systems. More particularly the present invention relates to optimizing defect detection sensitivity using structured illumination.

BACKGROUND

As demand for ever-shrinking semiconductor devices continues to increase, so too will the demand for improved semiconductor wafer inspection systems. The fabrication of semiconductor devices, such as logic and memory devices, typically includes processing a semiconductor wafer using a large number of semiconductor fabrication processes to form various features and multiple levels of the semiconductor devices. Multiple semiconductor devices may be fabricated in an arrangement on a single semiconductor wafer and then separated into individual semiconductor devices.

Various inspection system features and techniques have been employed to improve defect detection sensitivity for both reticles and wafers. One example is to decrease the wavelength of the illumination light that is being used to detect defects. As the wavelength decreases, smaller defects can generally be detected. However, there are limits to how short a wavelength can be used without the system configuration becoming too impractical, complex, or expensive. Another parameter of the inspection tool that affects defect detection sensitivity is the system's numerical aperture (NA). Unfortunately, the NA is often limited to a theoretical maximum of 1.0 for imaging in air or the system becomes too impractical to build and maintain.

There continues to be a need for improved systems and techniques for increasing sensitivity for defect detection.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one embodiment, a system for detecting defects in a semiconductor sample is disclosed. The system includes an illumination optics module for simultaneously scanning two or more structured illumination (SI) patterns across the sample in a scan direction. The two or more SI patterns have a phase shift with respect to each other, and the two or more SI patterns, e.g., which may be sinusoidal grating patterns, are aligned parallel to the scan direction. Said in another way, the two or more SI patterns are arranged in sequence along the scan direction. The system also includes a collection optics module for collecting output light from the sample in response to the SI patterns that are scanned across the sample and two or more detectors for individually detecting the output light collected for individual ones of the SI patterns. The system further comprises a controller operable to generate two or more SI images for the two or more SI patterns based on the individually detected output light and detect defects on the sample by performing a comparison type inspection process based on the two or more SI images.

In a specific implementation, the illumination optics module are configured for simultaneously scanning three structured illumination (SI) patterns across the sample in the scan direction, and the phase shift between the three SI patterns is ⅓ a cycle of the SI patterns. In another aspect, the number of SI patterns is selected so as to optimize defect detection coverage by the SI patterns. In another embodiment, the controller is further configured to cause the illumination optics module and the collection optics module to operate in a dark field inspection mode.

In one example, the illumination optics module is configured to generate the SI patterns on the sample by directing two sets of illumination beams from two opposite directions onto the sample, e.g., one from an azimuthal angle of 0 degree and the other from 180 degree, and the illumination beams of each of the two sets are phase shifted with respect to each other. The two sets of illumination beams also interfere with each other to produce the two or more SI patterns on the sample. In another aspect, the phase offset of the two or more SI patterns is fixed. In another example, the illumination optics module is configured to generate the SI patterns on the sample by directing two sets of illumination beams from orthogonal angles, for instance, including one from an azimuthal angle of 45 degree and the other from 135 degree, or one from 225 degree and the other from 315 degree, which is referred to as diagonal illumination.

In a specific implementation, the illumination optics module comprises (i) a coherent light source for generating an illumination beam, (ii) a first beam splitter for receiving the illumination beam and outputting the two or more illumination beams, (iii) a first collimator for receiving the two or more illumination beams from the splitter and bringing the two or more illumination beams into a parallel propagation, (iv) a phase-shifting splitter for receiving the two or more illumination beams from the first collimator and outputting a pair of split illumination beams for each of the two or more illumination beams, wherein the pairs of split illumination beams are phase offset relative to one another, (v) a second collimator for receiving the two or more pairs of split illumination beams, and (vi) illumination optics for directing towards the sample a first set of illumination beams that include a first one of each pair of split illumination beams and a second set of illumination beams that include a second other one of each pair of split illumination beams so as to form the two or more SI patterns on the sample. In a further aspect, the phase-shifting splitter is a diffractive optical element (DOE) and includes two or more beam splitting grating sections for the two or more illumination beams that are received by the DOE, and the two or more beam splitting grating sections have a phase offset relative to each other so as to cause the phase shift of the two or more SI patterns.

In another embodiment, the illumination optics module comprises (i) a coherent light source for generating an illumination beam, (ii) a first beam splitter for receiving the illumination beam and outputting the two or more illumination beams, (iii) a first collimator for receiving the two or more illumination beams from the splitter and bringing the two or more illumination beams into a parallel propagation, (iv) a splitter for receiving the two or more illumination beams from the first collimator and outputting a pair of split illumination beams for each of the two or more illumination beams, (v) a second collimator for receiving the two or more pairs of split illumination beams, and (vi) illumination optics for directing towards the sample a first set of illumination beams that include a first one of each pair of split illumination beams and a second set of illumination beams that include a second other one of each pair of split illumination beams, and the illumination optics include a first phase-shifting element for receiving the first set of illumination beams and a second phase-shifting element for receiving the second set of illumination beams. In this implementation, the first and second phase-shifting elements are configured to cause the first and second sets of illumination beams to be phase offset relative to one another so as to induce the phase offset for the two or more SI patterns on the sample.

In another aspect, the two or more SI patterns are spatially separate while being simultaneously scanned across the sample so as to be scanned over two or more spatially separate portions of the sample. In yet another embodiment, the illumination optics module is configured to direct two sets of phase-shifted illumination beams from diagonal directions towards the sample to form the two or more SI patterns on the sample, and the system further includes one or more rectangular apertures positioned at the pupil or Fourier plane of the collection optics, for example, to block certain diffraction orders and to reduce pattern noise in the image of semiconductor sample or wafer.

In another embodiment, the collection optics module further comprises one or more optical pupil filters to reduce noise due to ringing of imaging point spread function. In another aspect, the collection optics module further comprises a linear polarizer so as to modulate by a phase shift a signal detected by each detector. In yet another embodiment, the illumination optics module includes an immersion lens through which two sets of phase-shifted illumination beams are directed from opposite directions or orthogonal directions onto the sample so as to form the two or more SI patterns.

In an alternative embodiment the invention pertains to a method for inspecting a semiconductor sample. The method includes (i) simultaneously directing two or more structured illumination (SI) fringe patterns that are phase-shifted with respect to each other on a sample, (ii) scanning the two or more SI fringe patterns relative to the sample so that the two or more SI fringe patterns are aligned parallel to a scan direction, (iii) detecting spatially separated two or more output signals that each corresponds to an individual one of the two or more SI fringe patterns, (iv) generating an image from each of the two or more output signals, (v) comparing each generated image to a corresponding reference image to obtain one or more difference values and generate a defect image that includes one or more detected defects that each correspond to a difference value that is above a predetermined threshold, and (vi) merging the defect images from the two or more output signals, e.g., to get the entire defect map of the wafer.

In a specific example, comparing is accomplished by a die-to-die or cell-to-cell inspection process that includes defining a difference between each image and its corresponding reference image as a defect when the difference exceeds a predetermined threshold. In a further aspect, two or more different thresholds are used for the two or more SI images.

In another embodiment, the method includes subtracting a known fringe profile from each output signal so as to obtain a real defect signal. In another aspect, the two or more SI fringe patterns are spatially separate while being simultaneously scanned across the sample so as to be scanned over two or more spatially separate portions of the sample. In another aspect, the phase offset of the two or more SI patterns is fixed.

These and other aspects of the invention are described further below with reference to the figures.

DETAILED DESCRIPTION OF EXAMPLE EMBODIMENTS

Figure 1:
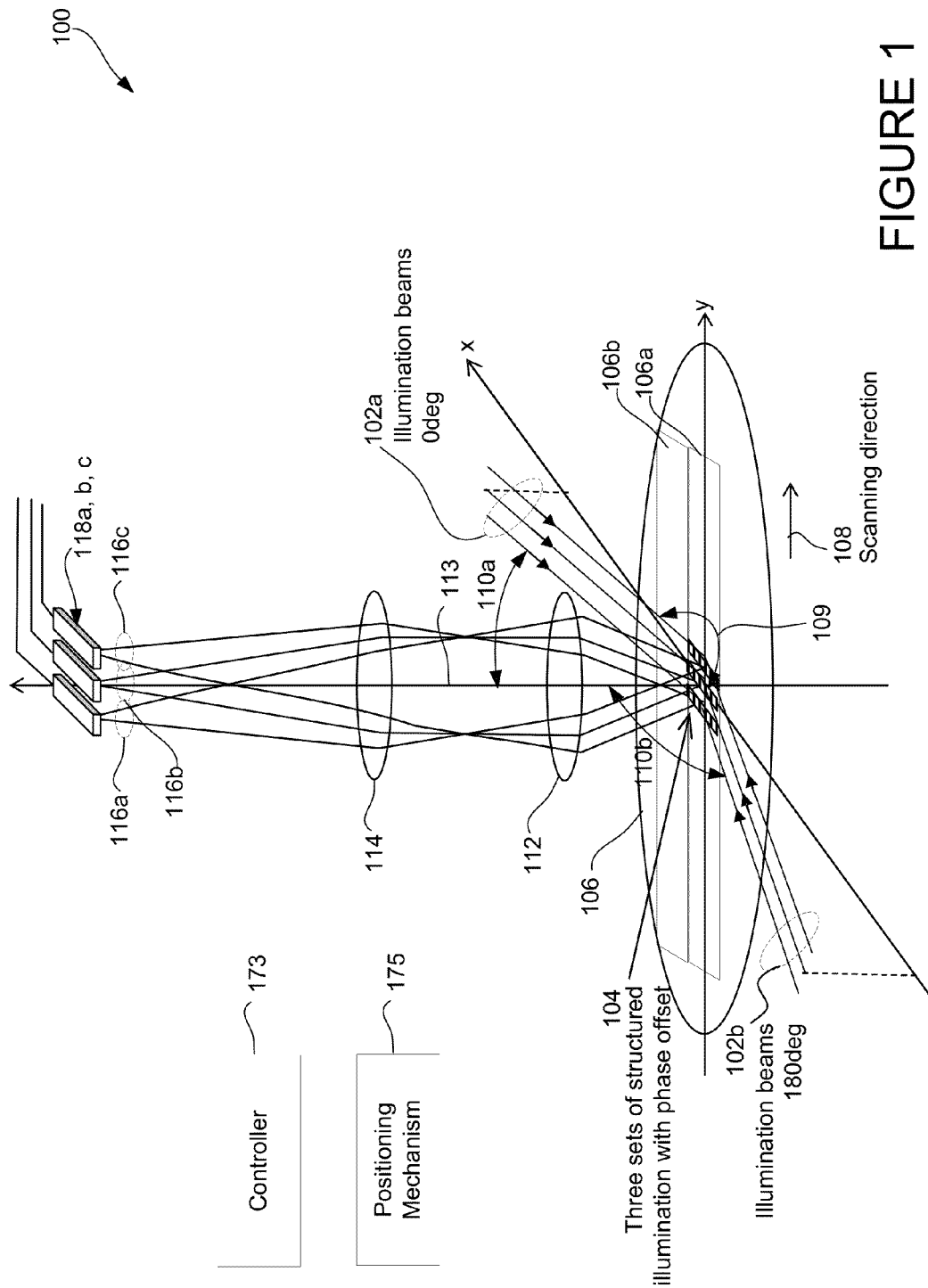
FIG. 1 is a diagrammatic representation of an inspection system that utilizes structured illumination in accordance with one embodiment of the present invention.

In the following description, numerous specific details are set forth in order to provide a thorough understanding of the present invention. The present invention may be practiced without some or all of these specific details. In other instances, well known component or process operations have not been described in detail to not unnecessarily obscure the present invention. While the invention will be described in conjunction with the specific embodiments, it will be understood that it is not intended to limit the invention to the embodiments.

Structured illumination (SI) can improve optical resolution beyond the Rayleigh limit of 0.61*wavelength/NA. In fluorescence applications, structure illumination (SI) generally involves three steps. First a grating fringe pattern can be projected on a sample surface, for example, by imaging a grating through the microscope objective lens. Multiple images can then be generated for each grating orientation at several different phase shifts (e.g., 3 or more) of projected grating, and then repeated for multiple grating orientations. A high resolution image can then be reconstructed from the multiple images, for example, by solving a linear system to derive two side bands in the Fourier domain and reverse Fourier transform the composite spatial spectrum (e.g., center and two side bands).

Certain embodiments of the present invention employ SI techniques to improve sensitivity for defect detection on semiconductor samples. Although an SI process and system may work well for fluorescence applications, in which imaging is incoherent and linear in intensity, the imaging properties of wafer inspection can be quite different and present certain challenges for implementation of a conventional SI technique to improve resolution in wafer inspection. Table 1 illustrates the differences between fluorescence imaging and wafer inspection imaging.

TABLE 1

Comparison between Fluorescence and Wafer Inspection Imaging

| Fluorescence Imaging | Wafer Inspection |
| --- | --- |
| Fluorescence | Elastic scattering |
| Incoherent | Coherent |
| Non-linear (for >2x) | Linear (for <2x) |
| Point source, isotropic | Pattern diffraction, highly directional |
| De-polarized | Strong polarization effect |

Certain semiconductor inspection modes are based on the comparison of identical features on the sample and anomalies are identified as defects, which is different from the requirements of fluorescence applications. In a semiconductor comparison type inspection, individual features do not need to be resolved since only feature differences are used. For instance, dies that are designed to be identical can be compared to each other to determine feature differences, which may be defined as candidate defects. Additionally, image reconstruction may not be suitable for wafer or reticle inspection because of its impact on cost and inspection speed, as compared the benefits that can be achieved from image reconstruction. Additionally, sequential scans with phase offset may be very difficult in practice because the phase shifts may be very difficult to control, adjust, and stabilize with respect to each other, especially for very short wavelengths, such as below 400 nm. Semiconductor inspections typically utilize a continuous scan of the sample to minimize inspection time. Accordingly, an SI approach would preferably be adapted to an inspection that implements continuous long range scan.

Certain embodiments of the present invention employ structure illumination (SI) systems and techniques to improve sensitivity for defect detection on semiconductor samples, such as wafers or reticles, by simultaneously scanning the sample with two or more different phase-shifted illumination fringe patterns in a single pass. Output light caused by the different phase-shifted illumination fringe patterns is then individually detected by spatially separated detectors and used to generate images. The two or more defect images can then be fused to get the entire defect map for the semiconductor wafer to detect all potential defects.

A higher number of fringe patterns may result in higher uniformity of defect detection coverage regardless of defect location. That is, a higher number of structured illumination patterns avoid missing defects having locations that coincide with only the dark fringes of the structured illumination patterns. However, these advantages are preferably balanced against incurring more cost and complexity by adding more detectors (e.g., optimizing the system performance to cost ratio).

Defect detection can be based on die-to-die (or cell-to-cell) comparisons without using image reconstruction so as to avoid the significant processing resource that may be required by image reconstruction. Additionally, certain embodiments can result in significant increases in signal-to-noise ratio (SNR) without the use of shorter wavelengths. These techniques and apparatus are especially useful in a dark field inspection mode as further described below.

The inspection system and techniques described herein may be implemented with respect to any suitable sample type. That is, the sample may be anything from which small defects need to be detected. Although the illustrated examples described herein relate to a sample that is in the form of a semiconductor wafer having a multitude of fine patterns thereon, the techniques and systems of the present invention may also be applied to a semiconductor reticle, a backside pellicle, a solar panel, a computer disk, etc.

FIG. 1 is a diagrammatic representation of an inspection system 100 that utilizes structured illumination in accordance with one embodiment of the present invention. The system 100 generally includes an illumination module (not shown) for generating a plurality of illumination beams that are phase shifted relative to each other. As shown, a first set of phase shifted beams 102a illuminate a sample 106 from a first azimuthal angle of 0 degree and polar angle of 110a, while a second set of phase shift beams 102b illuminate the sample 106 from a second azimuthal angle of 180 degree and polar angle 110b. In this case, the polar angles are the same as the incident angles. In the illustrated example, the first set of illumination beams and the second set of illumination beams are separated by an azimuthal angle 109 that is equal to 180 degrees. Together, the polar and azimuth angles define an illumination direction. The sample 106 is scanned in the direction 108 of y axis.

The system 100 may generate any number and type of phase offset illumination beams that form the two or more structured illumination patterns on the sample. For example, the two sets of phase offset illumination beams can take the form of three coherent laser beams that illuminate the sample surface from opposite directions. As a result of the two sets of three phase-shifted illumination beams, three sets of structured illumination patterns or interference fringes 104 are formed on the sample. The three sets of interference fringes have a fixed phase offset with respect to each other.

Figure 2:
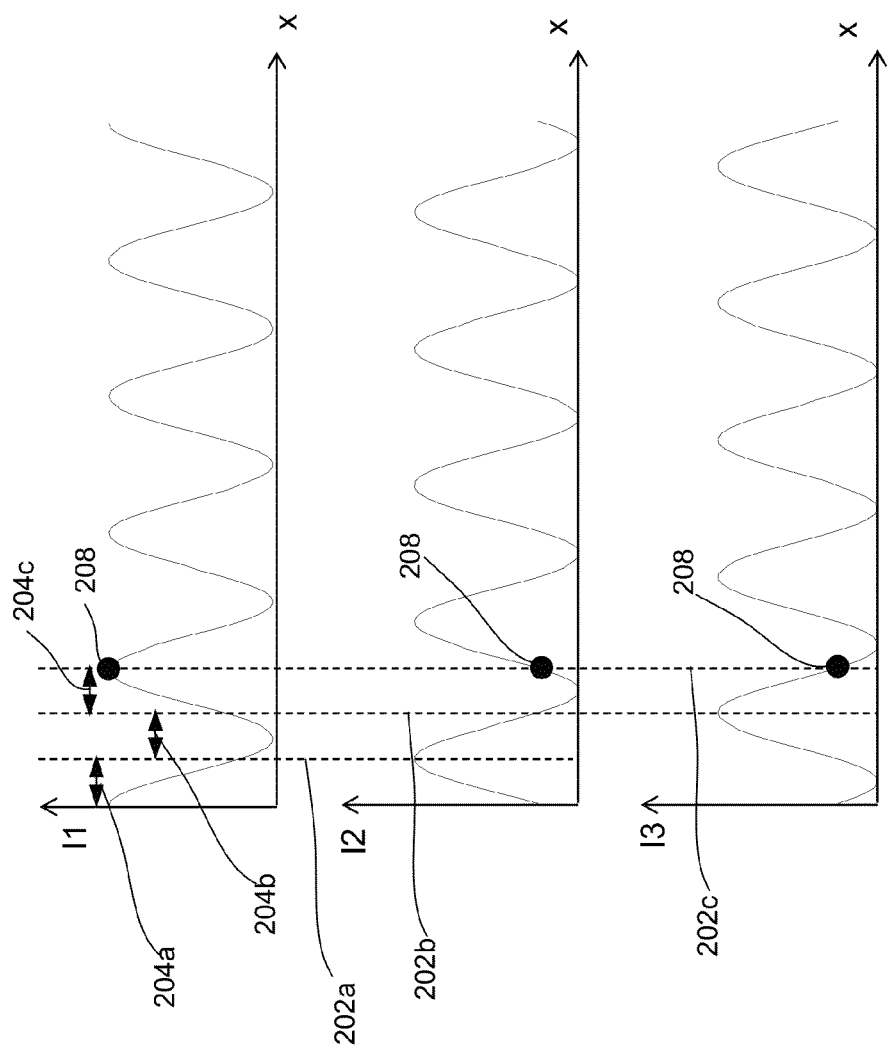
FIG. 2 illustrates an example intensity profile of three phase shifted illumination patterns in accordance with a specific implementation of the present invention.

FIG. 2 illustrates an example intensity profile of three phase shifted illumination patterns as a function of a sample position x, which is perpendicular to the sample scan direction (e.g., 108), in accordance with a specific implementation of the present invention. A second illumination pattern I2 is phase shifted from a first illumination pattern I1 by phase offset 204a, while a third illumination pattern I3 is phase shifted from the second pattern I2 by phase offset 204b. The first illumination pattern I1 is also effectively phase shifted from the third illumination pattern I3 by 204c if ignoring the full cycle of phase wrapping. Dashed line 202a corresponds to a peak of the second illumination pattern I2; dashed line 202b corresponds to a peak of the third illumination pattern I3; while dashed line 202c corresponds to a peak of the first illumination pattern I1. As shown, these peaks of the different illumination patterns are phase offset from each other. For example, the cycle of the second pattern I2 is shifted by ⅓ of the fringe cycle relative to the first pattern I1, and the cycle of the third pattern I3 is shifted by /1;3 of the fringe cycle relative to the second pattern I2. Note fringe patterns I1, I2, and I3 have the same fringe cycle.

The illumination optics column may be moved respect to the sample stage and/or the stage moved relative to the illumination optics by any suitable positioning mechanism 175 so as to scan the SI patterns across portions of the sample. For example, a motorized stage may be utilized to move the sample. A motorized stage may be formed from a screw drive and stepper motor and ball bearing stage or air bearing stage, linear drive with feedback position, or band actuator and stepper motor, by way of examples. One or more positioning mechanisms may also be configured to move other components of the inspection system, such as the aperture modules, illumination or collection mirrors, wavelength filters, polarizers, etc.

The structured illumination patterns may be scanned across individual swaths of the sample. As shown, three structured illumination patterns 104 are scanned across swath 106a in scan direction 108. These illumination patterns 104 may then be scanned across another swath 106b in a scan direction that is opposite to the first swath's scan direction 108 so that a serpentine scan pattern is implemented. Alternatively, the structured illumination patterns may be scanned across the sample with any suitable scan pattern, such as a circular or spiral scan pattern. Of course, the sensors may have to be arranged differently (e.g., in a circular pattern) and/or the sample may be moved differently (e.g., rotated) during scanning in order to scan a circular or spiral shape from the sample.

The illumination from the light source may also pass through a number of lenses which serve to relay (e.g., shape, focus or adjust focus offset, filter/select wavelengths, filter/select polarization states, resize, magnify, reduce distortion, etc.) each illumination beam towards the sample.

Any suitable collection optics may be used to collect output fringe patterns from the sample in response to a plurality of structured illumination patterns directed onto the sample. Referring back to the system illustrated FIG. 1, the light 116a, 116b, and 116c scattered by the sample 106 from the different illumination field of the three sets of phase offset structured illumination fringes formed by 102a and 102b are collected by collection optics (e.g., lens 112 and 114) and combined so that individual output light patterns corresponding to the phase-shifted SI patterns are individually directed onto different detectors (e.g., 118a, 118b, and 118c). That is, the three sets of fields illuminated by the three sets of SI fringes formed by the three output beams 116a~116c are imaged by objective lens 112 and magnification lens 114 onto three separate sensors 118a~118c. Sensors 118a, 118b, and 118c are preferably time delay integration (TDI) detectors. The SI fringes are parallel to the sample scan direction, which is also the TDI integration direction. Therefore, the fringe contrast is preserved. The outputs of three TDI sensors correspond to the three separate illumination fields of SI fringes have a fixed phase offset. Any suitable type of 2D imaging sensor may be used in place of TDI sensors, if sample is moved in a step and flash fashion rather than at a continuous constant speed, for example.

Figure 3:
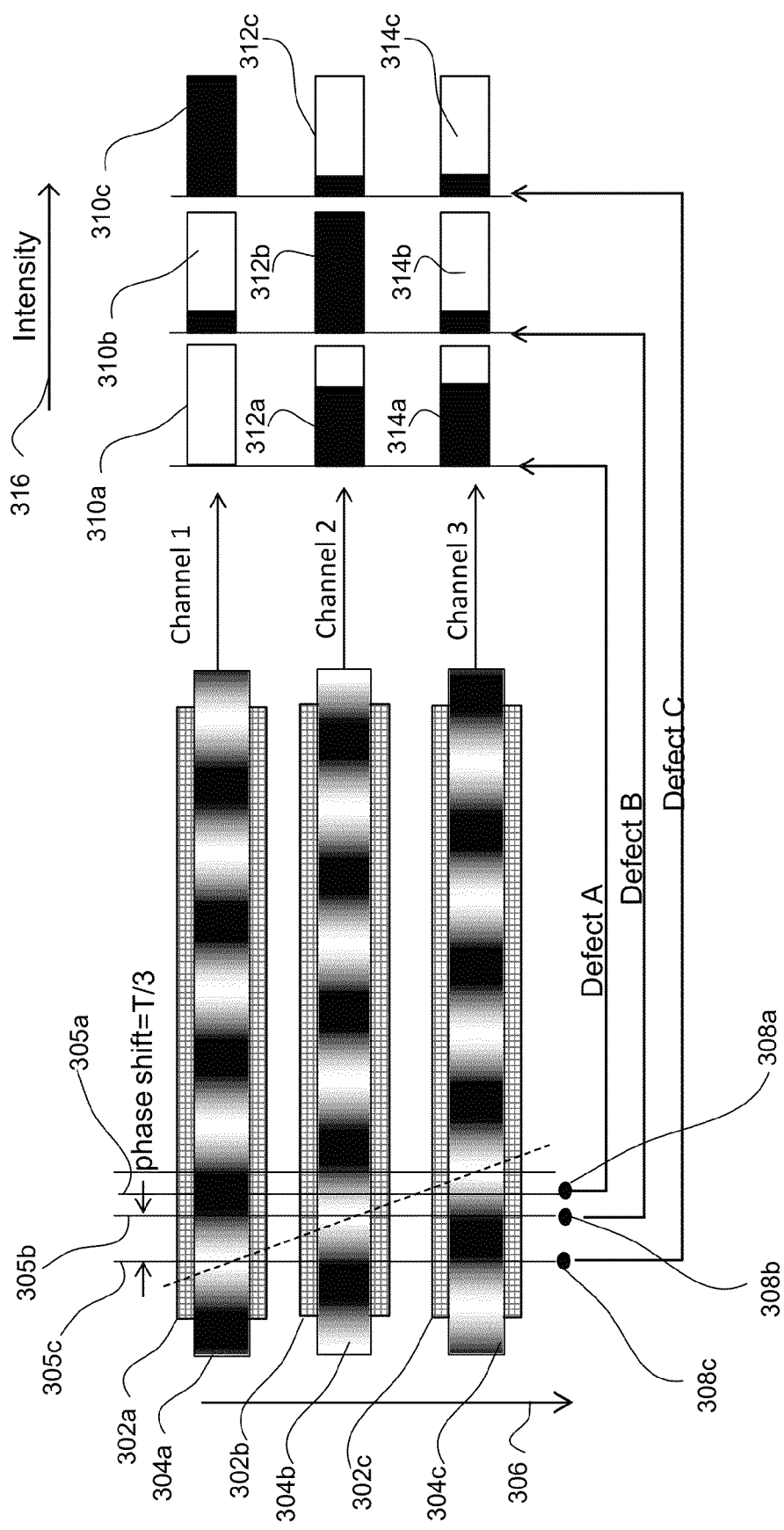
FIG. 3 illustrates detection of three defects using three detectors that are arranged to receive an output beam in response to three simultaneously scanned structured fringe patterns in accordance with one example application of the present invention.

In the example illustrated below, as the sample moves past the sensors, light is detected from individual swath portions, onto which the individual structured patterns are scanned. FIG. 3 illustrates detection of three defects using three detectors 302a, 302b, and 302c that are arranged to receive output patterns in response to three simultaneously scanned illumination patterns 304a, 304b, and 304c in accordance with one example application of the present invention.

A defect's position relative to each illumination pattern will affect such defect's output intensity as sensed by each detector. Although the following examples depict a high intensity value as a defect and a low intensity as background noise, the relative intensity values that correspond to defects and background can be reversed, such that a low intensity value corresponds to a defect. In the illustrated embodiment, defects 308a, 308b, 308c have different locations relative to the three illumination patterns 304a, 304b, and 304c. If an illumination pattern's peak (or particular point on the peak's slope) is scanned over a defect's location, the defect will be sensed at a higher intensity relative to the background of the sample, as compared to other illumination patterns' non-peaks or valleys being scanned over the defect. For instance, a defect 208 (see FIG. 2) that is at position 202c relative to the three illumination patterns I1~I3 will have a highest intensity for illumination pattern I1 since the defect is positioned at a location that is scanned by a peak of such illumination pattern I1. In contrast, the same defect 208 will have a lower intensity for illumination patterns I2 and I3 since a lower point (relative to the peak intensity of I1) in the illumination signals I2 and I3 is scanned over such defect 208.

Referring back to FIG. 3, defects 308a~308c are located at positions 305a~305c, respectively, and such positions are shown relative to peak and valley portions of the illumination patterns 304a~304c. The peaks are illustrated as a white, while the valleys are represented as black with shades of gray there between. The output intensity levels 310a~c, 312a~c, and 314a~c for each defect position and detector channel are shown as increasing in direction 316. A completely filled rectangle 310c corresponds to a maximum output intensity level for each defect location, while a completely white rectangle 310a indicates a minimum output intensity level for each defect location.

Defect 308c will result in a maximum intensity output 310c for detector 302a and a small levels of intensity (312c and 314c) at the other detectors 302b and 302c since such defect's position 305c corresponds with a peak of the illumination pattern 304a and a lower signal level of the other illumination patterns. Likewise, defect 308b at position 305b will result in maximum intensity 312b for detector 302b and relatively smaller intensity levels (310b and 314b) for detectors 302a and 302c. Defect 308a at position 305a will result in significant intensity levels 312a and 314a for detectors 302b and 302c with a lowest intensity 310a for detector 302a.

Referring back to FIG. 1, the signals captured by each sensor (e.g., 118a~c) can be processed by a computer system 173 or, more generally, by one or more signal processing devices, which may each include an analog-to-digital converter configured to convert analog signals from each sensor into digital signals for processing. The computer system 173 typically has one or more processors coupled to input/output ports, and one or more memories via appropriate buses or other communication mechanisms.

The computer system 173 may also include one or more input devices (e.g., a keyboard, mouse, joystick) for providing user input, such as changing thresholds, wavelengths, and other inspection recipe parameters. The computer system 173 may also be connected to the stage for controlling, for example, a sample position (e.g., focusing and scanning) and connected to other inspection system components for controlling other inspection parameters and configurations of such inspection system components.

The computer system 173 may be configured (e.g., with programming instructions) to provide a user interface (e.g., a computer screen) for displaying resultant intensity values, images, and other inspection results. The computer system 173 may be configured to analyze intensity, phase, and/or other characteristics of the reflected and/or scattered sensed light. The computer system 173 may be configured (e.g., with programming instructions) to provide a user interface (e.g., on a computer screen) for displaying resultant intensity values, images, and other inspection characteristics. In certain embodiments, the computer system 173 is configured to carry out inspection techniques detailed herein.

Because such information and program instructions may be implemented on a specially configured computer system, such a system includes program instructions/computer code for performing various operations described herein that can be stored on a non-transitory computer readable media. Examples of machine-readable media include, but are not limited to, magnetic media such as hard disks, floppy disks, and magnetic tape; optical media such as CD-ROM disks; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

Figures 4A, 4B:
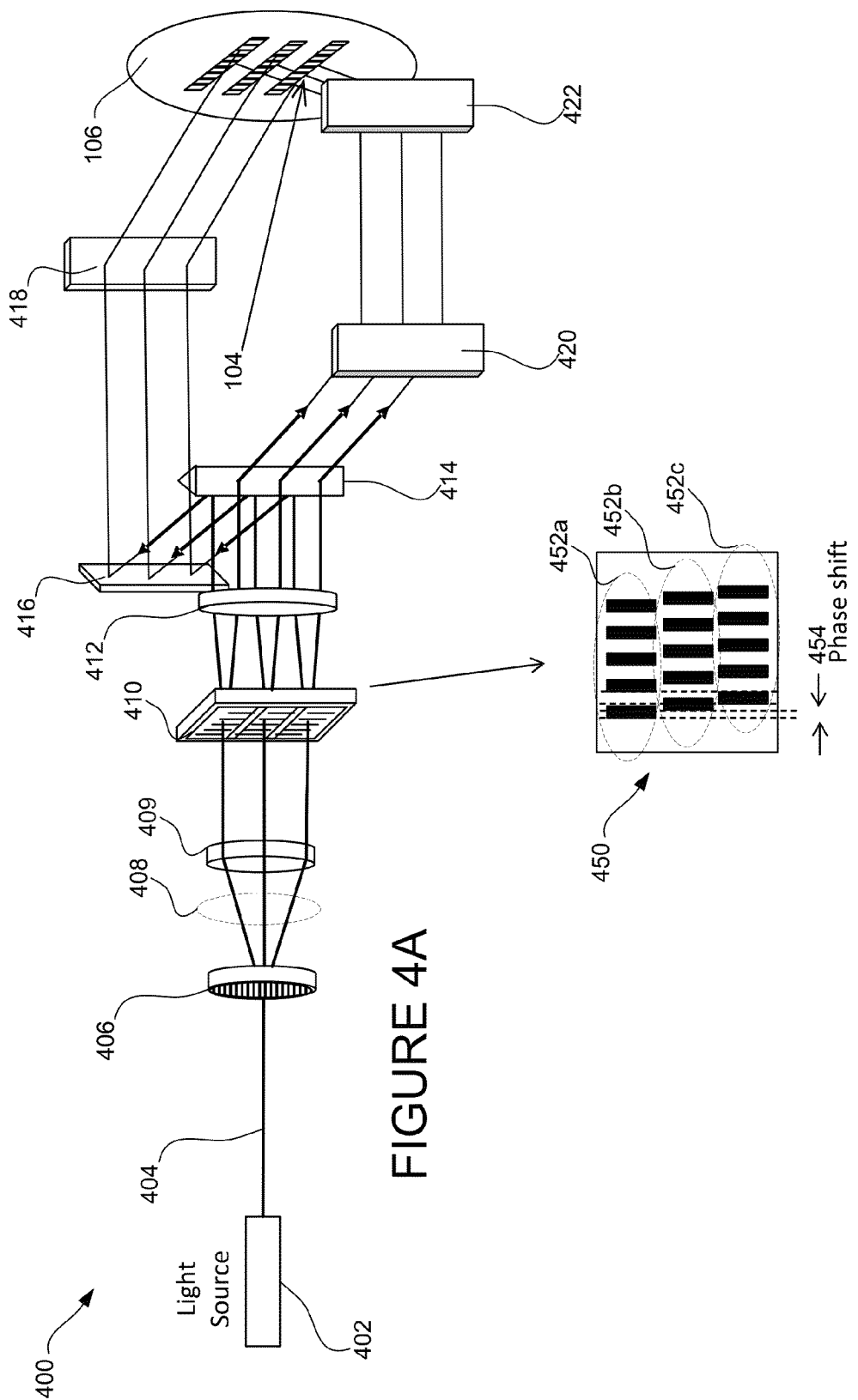
FIG. 4A is a diagrammatic representation of a specific illumination module of an inspection system in accordance with one embodiment of the present invention.
FIG. 4B is a diagrammatic view of a phase shifting diffractive optical element (DOE) in accordance with one example implementation.

FIG. 4A is a diagrammatic representation of a specific illumination module 400 of an inspection system in accordance with one embodiment of the present invention. As shown, a light source 402, such as a laser, may generate an illumination beam 404, which is received by a first beam splitter 406, such as a DOE, which splits the illumination beam 404 into three individual illumination beams 408. The three illumination beams 408 may then be received by collimator 409, which is configured to collimate the three beams 408. The collimator is arranged and dimensioned to bring the illumination beams 408 into parallel propagation.

Examples of light sources include a laser, laser-driven light source, a high-power plasma light source, a filtered lamp, LED light sources, etc.

A phase shifting beam splitter 410, such as a DOE, may then be arranged to receive the collimated illumination beams. The DOE is further dimensioned and positioned to split each of the received three beams into a pair of beams. The two or more DOE beam splitters are displaced with respect to each other, causing a fixed phase shift among the two or more split beams. While the split beams are recombined on the semiconductor wafer, they interfere with each other and two or more structured illumination fringe patterns are formed with the same amount of phase shift as the two or more DOE elements are arranged.

The phase shifting splitter 410 may include a section of beam splitting grating for each received illumination beam. For the illustrated example, a phase shifting DOE includes three sections of beam splitting gratings for the three received illumination beams. The different beam splitting gratings may have a phase shift with respect to each other (e.g., shifted by ⅓ of the grating cycle for three illumination beams).

The FIG. 4B is a diagrammatic view of a phase shifting diffractive optical element (DOE) 450 in accordance with one example implementation. In general, the phase-shifting DOE 450 is positioned and dimensioned to generate two beams for each received illumination beams. As shown, three different gratings 452a, 452b, and 452c are offset in position with respect to each other (e.g., 454), which introduces a phase shift in the diffracted/split beams that is proportional to the position offset of grating.

The three phase-shifted pairs of illumination beams may then be collimated by collimator 412. Any suitable number of illumination optics may then be used to split each pair into two different sets and direct such two different sets of phase-shifted illumination beams towards the sample at two different angles (e.g., 0 and 180 degrees) so as to form three different illumination patterns 104 on the sample 106. As shown, a prism shaped mirror 414 receives the pairs of three phase-shifted illumination beams and redirects such beams into two different sets of three illumination beams. Mirrors 416 and 418 are arranged to direct a first set of phase-shifted illumination beams towards the sample 106, while mirrors 420 and 422 are arranged to direct a second set of phase-shifted illumination beams towards the sample 106 from a direction that is opposite the first set of phase-shifted illumination beams.

Figure 4C:
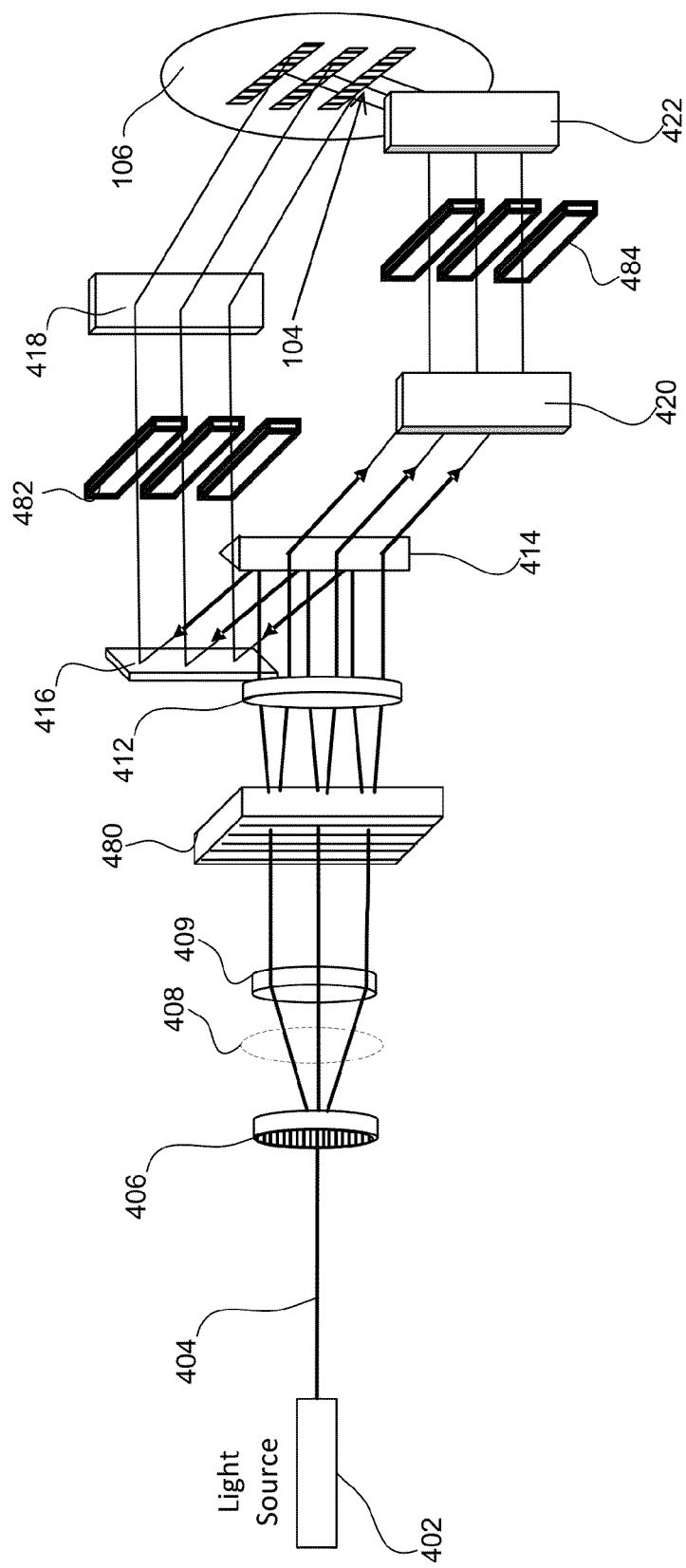
FIG. 4C is a diagrammatic representation of an illumination module of an inspection system having an alternative phase shifting arrangement in accordance with an alternative embodiment of the present invention.

A phase-shifting element may be positioned at any suitable position in the illumination beam path, as an alternative to being incorporated into the splitter DOE 410. FIG. 4C is a diagrammatic representation of a specific illumination module of an inspection system in accordance with an alternative embodiment of the present invention. In this embodiment, a beam splitter 480 may be positioned to receive each of the three illumination beams output from collimator 409 and output a pair of split illumination beams for each of the three illumination beams. The pairs of illumination beams may then be directed by optics elements that are similar to the elements of FIG. 4A so as to generate a first and a second set of three phase-shifted illumination beams.

Phase-shifting elements 482 and 484 may also be placed in each of the paths of the two sets of illumination beams. The phase-shifting elements may be placed at other collimated positions (such as between prism 414 and mirror 420 and between prism 414 and mirror 416), other than the positions that are illustrated. The phase-shifting elements 482 and 484 could be a set of three glass plates having different thickness to introduce a different phase delay of each of the three beams passing through. The phase-shifting elements 482 and 484 could also be movable mirrors of electro-optical phase modulators to cause optical path difference between the two sets of split beams and to provide an adjustable phase shift between the illumination fringes patterns on sample.

Regardless of the particular illumination configuration, the split two sets of phase-shifted illumination beams are directed towards the sample at incident angles relative to the normal axis (e.g., 113), which are the same as the polar angles in this illustration. The two splits sets of illumination beams recombine at the sample surface to form three spatially separated sets of interference fringes to provide structured illumination on three separate regions of the sample. The phase shift of the three structured illumination patterns are determined by the phase offset of the three sections of the grating on the one or more phase-shifting elements (single DOE 410 or phase shift elements 482 and 484).

The incident angles of the two sets of illumination beams are selected to result in particular pitch sizes for the interference illumination patterns that are incident on the sample. The following equation may be used to derive the pitch for the intensity of structured illumination fringes:

$$\Lambda = \frac{\lambda}{2n\sin\theta}$$

where $\Lambda$ is the period for the intensity of structured illumination, $\theta$ is the incident angle, $\lambda$ is the wavelength, and n is the index of refraction of the incidence medium. For instance, for a structured illumination configuration with immersion lens, n is the refractive index of the immersion material. For conventional imaging in air, n is approximately 1. In general, a shallower incident angle (with respect to the sample surface) results in a smaller pitch. Smaller pitches have the advantage of increased defect sensitivity since small pitch fringe results in higher contrast between a small defect and its adjacent pattern background.

The illumination fringes for the three regions are parallel to each other, and are all oriented to be parallel to the detector scan direction such that the integration along the detector scan direction does not average out the fringe contrast. Fringe contrast pertains to the ratio of the difference to the sum of maximum and minimum fringe intensities.

Additionally, the illumination module is configured to produce fringe patterns with phase offsets that are fixed and insensitive to phase shift errors. In contrast, systems that are designed to sequentially scan phase-offset fringe patterns would have difficulties maintaining the phase offset between different scans. For instance, an illumination fringe cycle that is ½ the illumination wavelength and a ⅓ cycle offset of less than 50 nm would be extremely difficult to maintain in a system that sequentially scanned these phase offset fringes across the channel.

It should be noted that the interference fringes of two illumination beams are directed outside the imaging NA for dark field configurations so that the fringes are not resolvable at a detector plane. FIGS. 4A and 4C are illustrations of the phase shift between the illumination patterns and is not meant to show that the fringes are actually visible on the detector plane.

Defects can be identified by conventional defect detection algorithms, such as a simple thresholding following a die-to-die comparison for larger pattern structures that are resolvable by the imaging optics, or a simple thresholding without die-to-die for small pattern structures that are not resolvable, which only results in a uniform background. Defect maps from three channels can then be merged to avoid missing defects that would otherwise be missed using a single channel detection because the defects are located at the dark fringes of illumination. This technique is a very different concept from conventional structured illumination, where images have to be reconstructed by two steps of Fourier transforms. Certain embodiments of the present invention do not require and do not reconstruct images via Fourier transforms.

More sophisticated algorithms can further improve defect detection. For example, the peak signal from the three channels can be fitted to known illumination fringe profile so that the real defect signal can be subtracted out from the known illumination fringe profile to obtain the "real" defect signal. Additional statistical information can be used to improve defect capture rate and lower the false count, and also to provide more accurate position information of the defects.

Figure 5A:
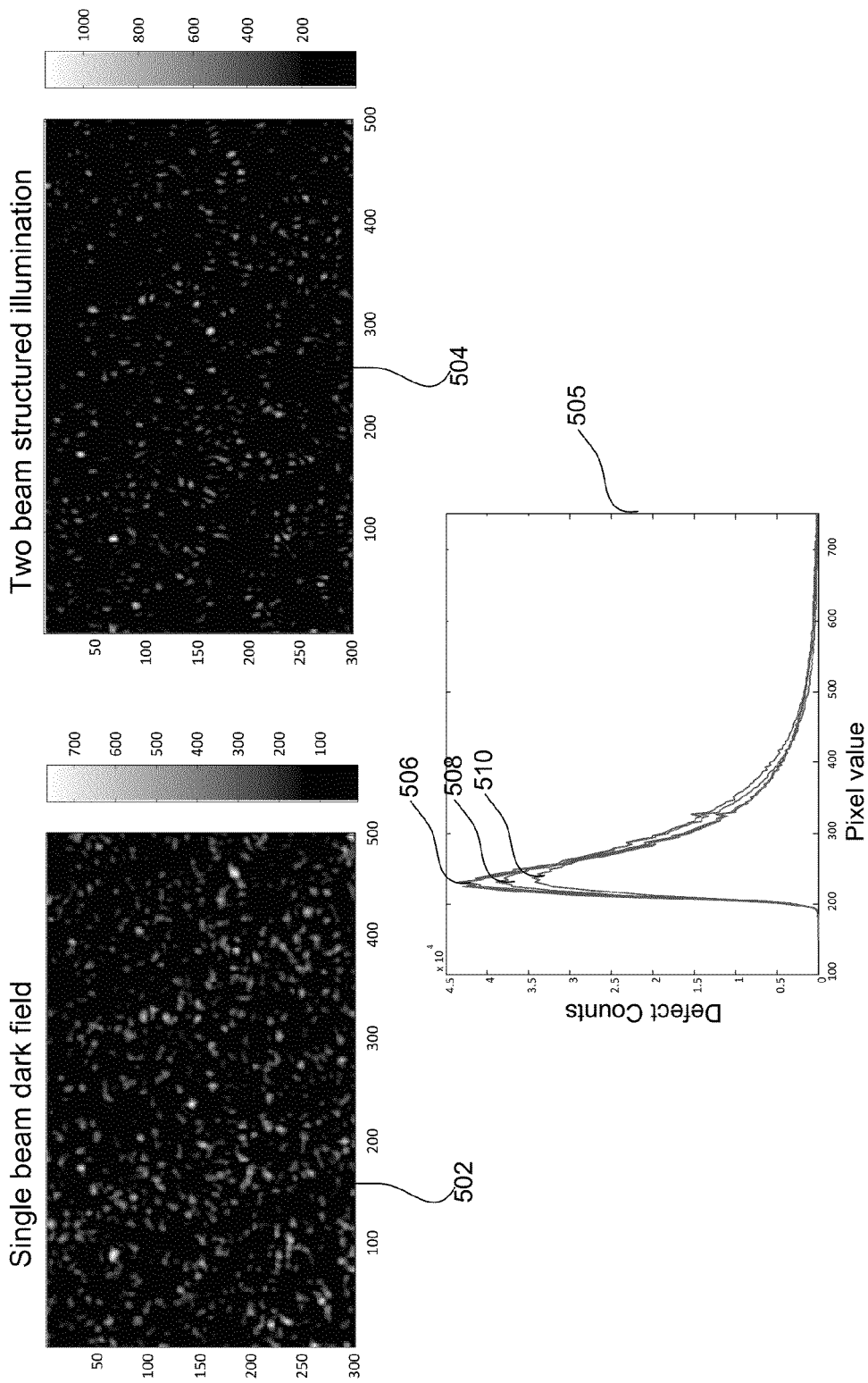
FIG. 5A shows example background noise images that are captured from a single oblique illumination beam and structured illumination using two coherent oblique beams in accordance with one embodiment of the present invention.
Figure 5B:
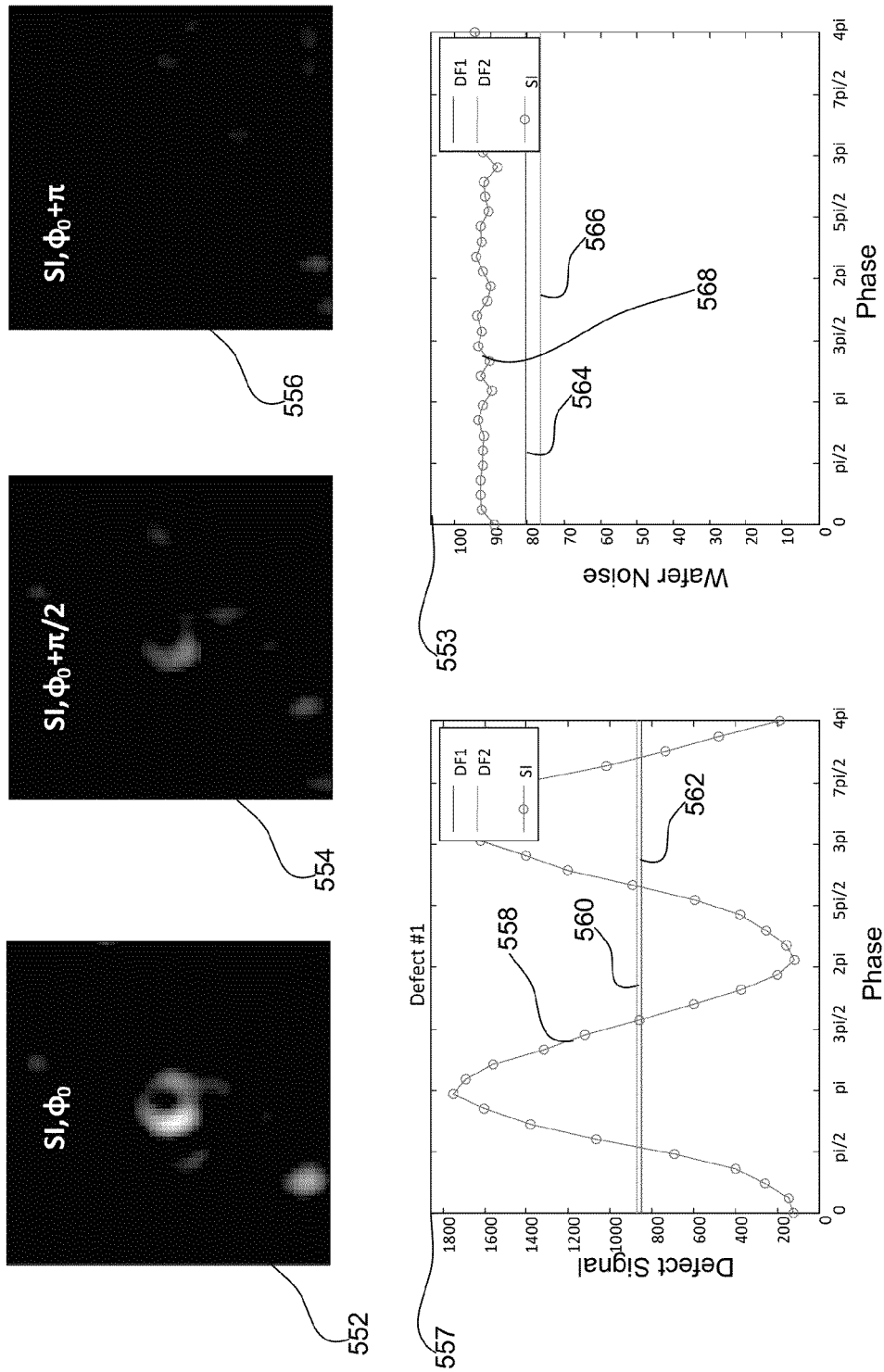
FIG. 5B illustrates defect and noise signals for different illumination patterns in accordance with a specific implementation of the present invention.

FIGS. 5A and 5B illustrate the principle of signal-to-noise ratio (SNR) enhancement for a small particle on a polysilicon wafer using certain embodiments of the present invention. FIG. 5A shows example background noise images that are captured from a single oblique illumination beam and structured illumination using two coherent oblique beams in accordance with one embodiment of the present invention. The background noise image 502 resulting from a single coherent illumination beam in dark field mode contains mostly speckle noise. The noise image 504 for structured illumination patterns (also in dark field mode) from two sets of coherent oblique illumination beams contain roughly the same noise as the noise image for the single oblique illumination beam.

Because the illumination beams are outside of the imaging NA, there is no visible fringe patterns in the structured illumination images, and the modulation of random surface is smoothed out by the imaging pupil. Graph 505 illustrates pixel counts of background noise as a function of pixel value (or intensity value). The graph also includes the histogram plots of background noise for a single illumination beam at 0 degrees (510), a single illumination beam at 180 degrees (508), and a structured illumination pattern (506). The plots show that the noise distributions for all three illumination modes are essentially the same.

FIG. 5B illustrates defect and noise signals for different illumination patterns in accordance with a specific implementation of the present invention. The defect image 552 was obtained from a first structured illumination pattern; defect image 554 was obtained from a second structured illumination pattern that is phase offset from the first pattern by $+\pi/2$; and defect image 556 was obtained from a third structured illumination pattern that is phase offset from the first pattern by $+\pi$.

The defect signal of a small particle is modulated by the illumination fringe pattern. The donut shape image (shown clearly in image 552) of a small particle is a result of the scattering characteristics of small particle under P polarized illumination. The intensity of the defect changes from maximum to minimum when illumination fringe is phase shifted by 180 degrees. As shown in plot 557, the defect signal 558 for an SI image oscillates with illumination phase shift, while the defect signals (560 and 562) for individual beams remain flat. As shown in plot 553, the noise signal 568 for the SI image remains mostly constant, as compared with the individual beam noise signals 564 and 566, and they are about the same. Generally with enough number of images at different phase offsets, the maximum signal can always be captured so as to provide about 2× improvements of SNR.

Figure 5C:
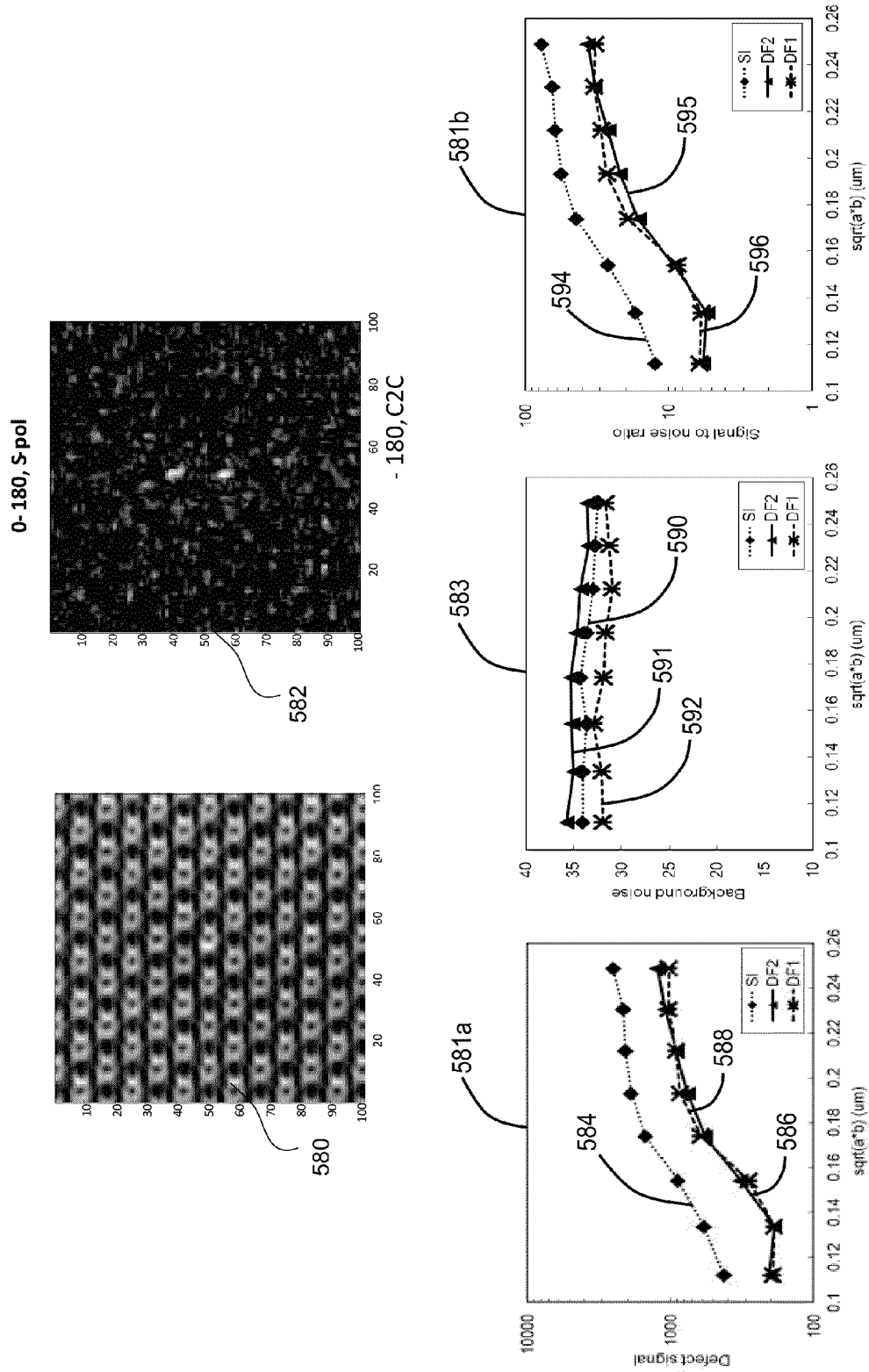
FIG. 5C illustrates signal-to-noise ratio (SNR) improvements for structured illumination patterns that are scanned simultaneously over a sample area having defects.

FIG. 5C illustrates signal-to-noise ratio (SNR) improvements for structured illumination patterns that are scanned simultaneously over a sample area having defects. The top left image 580 is the raw wafer image under structured illumination, and the top right image 582 is the image after cell-to-cell subtraction of one of the set of programmed defects. Defect signals plots 581a and 581b and noise plot 583 illustrate defect and noise signals, respectively, as a function of the square root of the area (a×b) of the detect.

The SNR improvement is consistently 2× over the conventional single beam dark illumination for all defect sizes tested. As shown, the defect signal 584 from the structured illumination patterns is 2× higher than the defects signals for single oblique beams 586 and 588, which are directed from opposite directions from each other. In addition, the background noise 590 for the structured illumination patterns remains relatively the same, as compared with the noise 591 and 592 for the two single illumination beams. Therefore the signal-to-noise ratio (SNR) of structured illumination 594 is 2× of the single beam illumination 595 or 596 for all defect sizes.

Figure 6:
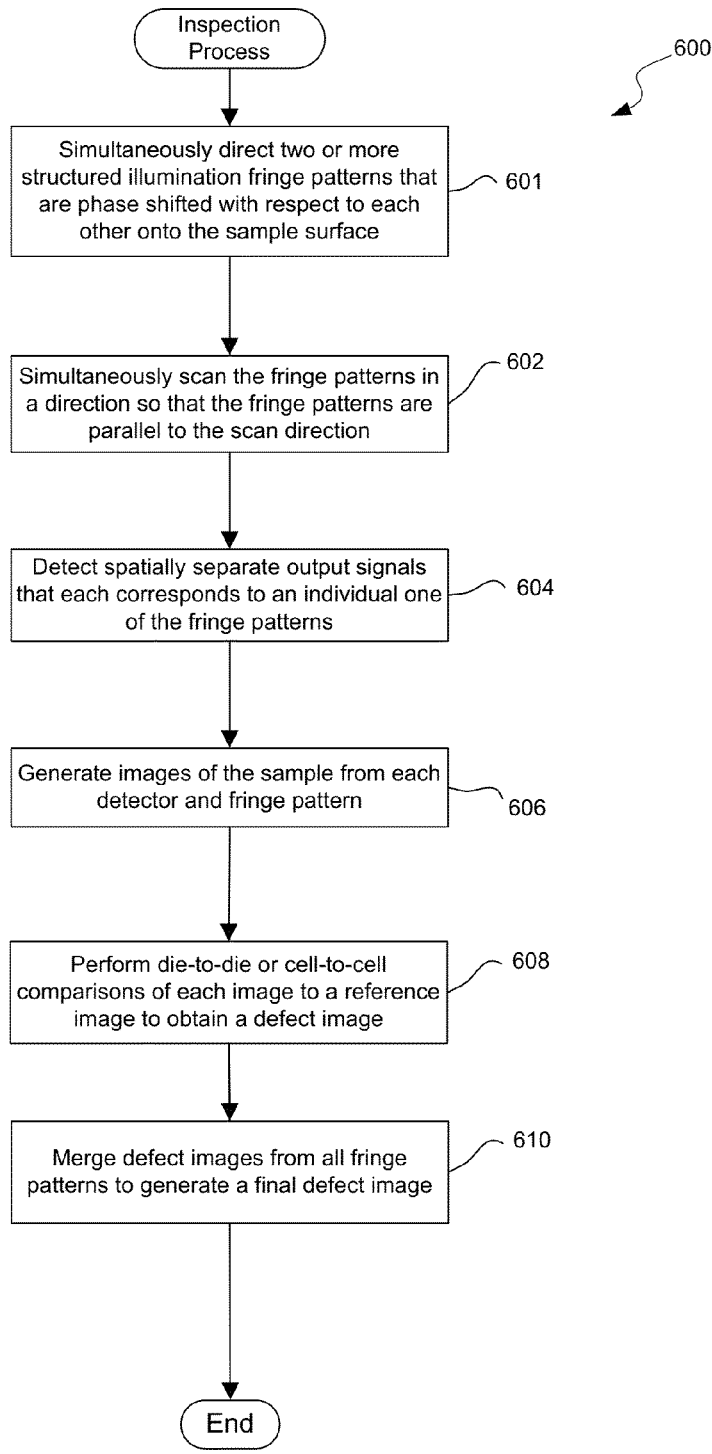
FIG. 6 is a flow chart illustrating an inspection procedure utilizing structured illumination to detect defects in a semiconductor sample in accordance with one embodiment of the present invention.

FIG. 6 is a flow chart illustrating an inspection procedure utilizing structured illumination to detect defects in a semiconductor sample in accordance with one embodiment of the present invention. Initially, two or more structured illumination fringe patterns that are phase shifted with respect to each other may be simultaneously directed onto the sample surface in operation 601. These fringe patterns may be simultaneously scanned in a direction so that the fringe patterns are parallel to the scan direction in operation 602.

Spatially separate output signals that each corresponds to individual ones of the fringe patterns may then be detected in operation 604. Images of the sample may then be generated from each detector and fringe pattern in operation 606. A die-to-die or cell-to-cell comparison of each test image to a reference image may then be performed to obtain a defect image in operation 608. For instance, the difference between the test and reference image may be defined as a defect if such difference is above a predetermined threshold. The defect images from all fringe patterns may then be merged to generate a final defect image in operation 610.

Test images and reference images may be obtained from portions of the sample that are designed to be identical. Alternatively, reference images may be simulated from the design database.

Individual thresholds for defect detection can be applied to difference values between the test images/signals and individual reference images/signals for individual channels or detectors. For instance, a defect can be detected for each detector when a particular intensity difference threshold is reached. The thresholds that are applied for the different detector signals may be the same or different values.

The above described systems can be altered in various ways and not depart from the intent of the invention. In an alternative system embodiment, diagonal illumination is combined with a rectangle aperture (e.g., in the collection optics module) to further reduce background noise for pattern wafer inspection. Diagonal illumination can be achieved by directing the incidence beam from azimuth angles of 45 and 135 degrees, or from 225 and 315 degrees, instead of 0 and 180 degrees. In another embodiment, optical pupil filters (Fourier filter and apodizers) can be used in the collection optics module. Structured illumination may need more Fourier bars than single beam illumination, but it does not exclude the use of Fourier filters. Fourier filters can be used to block certain diffraction orders and, as a consequence, reduce the pattern noise and increase defect sensitivity. Apodizers can be used to reduce the coherent noise due to ringing of imaging point spread function.

Figure 7:
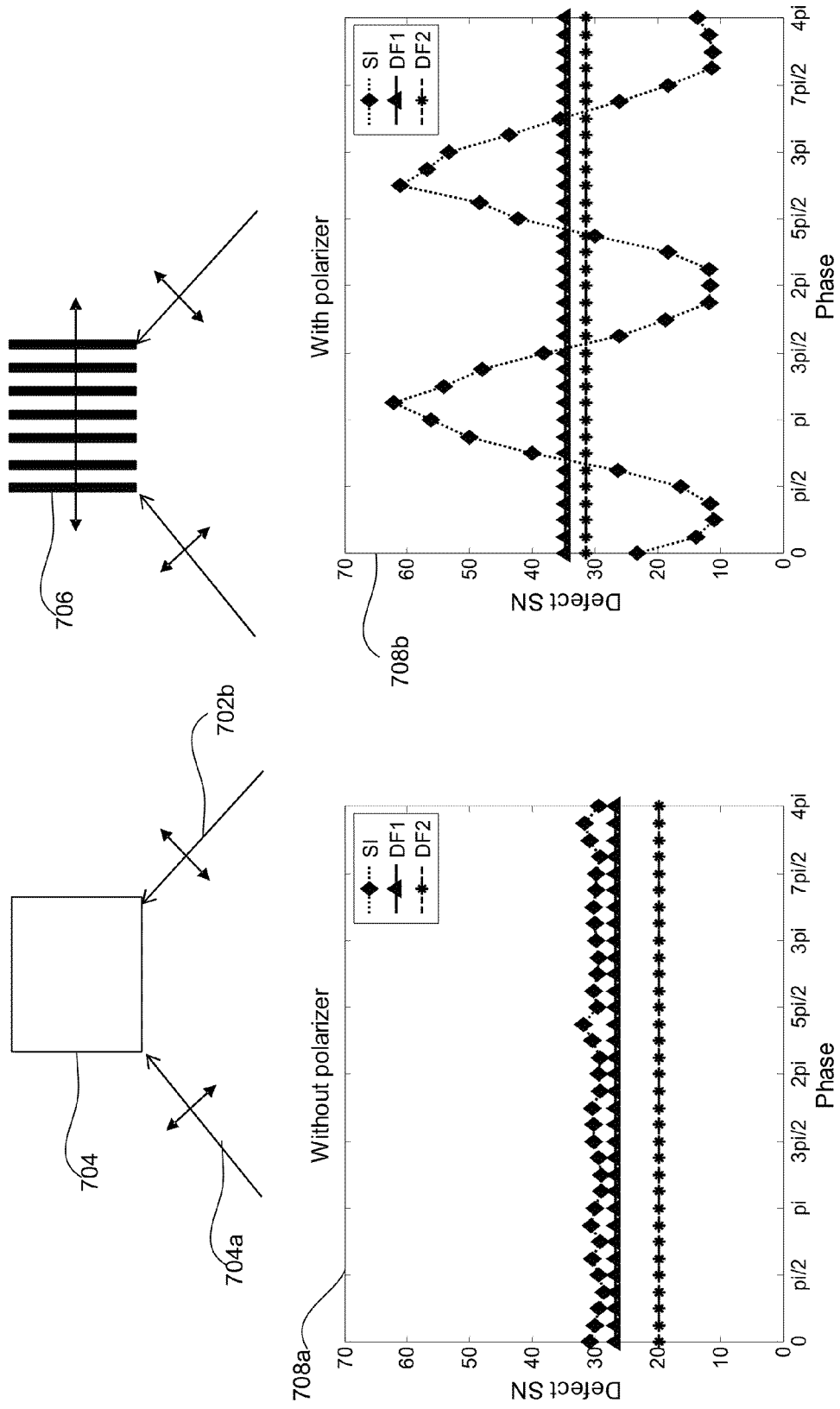
FIG. 7 illustrates use of a polarizer in accordance with an alternative implementation of the present invention.

FIG. 7 illustrates use of a polarizer in accordance with an alternative implementation of the present invention. Diagonal illumination angles can be very effective in reducing pattern noise caused by horizontal or vertical lines, and a rectangle aperture (e.g., at the pupil plane of the collection optics) may be used when imaging NA is large (about >0.7). The polar angle of oblique illumination beams, e.g., 704*a* and 704*b*, is generally very large, often greater than 70 degrees from wafer surface normal. The azimuthal angle separation between the two 45 degrees illumination beams is 90 degrees. For S polarization of illumination, the electrical field of the two incident beams can be nearly perpendicular to each other so as to cause no interference patterns (704) to be generated on the sample so as to result in no signal-to-noise improvement of structured illumination to single beam oblique illumination as shown in plot 708*a*.

For S illumination and unpolarized detection, there is no signal modulation as there is no interference fringes on wafer. By adding a linear polarizer to the imaging path, the signal will modulate by the interference of the polarization components defined by the polarizer in imaging path to be parallel, which also carry the phase modulation of the illumination (706) so as to result in increased defect signal-to-noise for structured illumination, for example, as shown by plot 708*b*.

Figure 8:
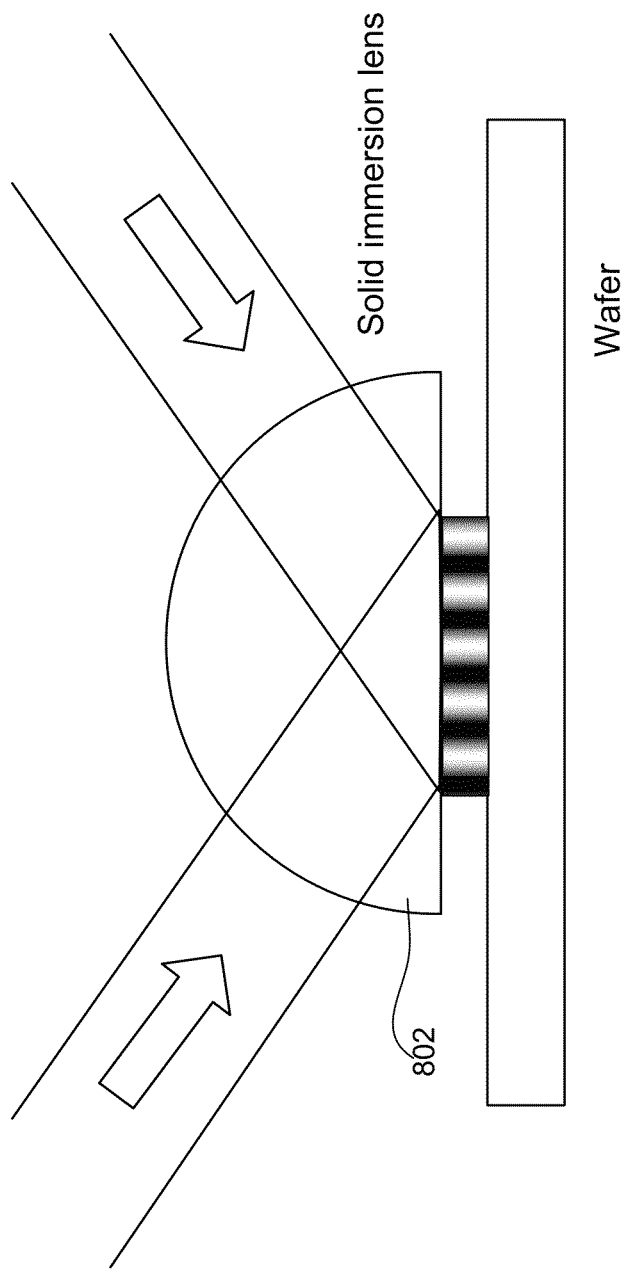
FIG. 8 illustrates an inspection system portion that includes a solid immersion lens in accordance with another alternative embodiment of the present invention.

Illumination fringe frequency can be further increased by using immersion lens, solid or liquid. For liquid immersion lens, the fringe frequency may increase by a factor of the matching liquid index. That is, the refractive index of the liquid or solid immersion lens can be selected to make the pattern pitch smaller. FIG. 8 illustrates an inspection system portion that includes a solid immersion lens 802 in accordance with another alternative embodiment of the present invention. The illumination beams are directed through this immersion lens onto the sample. For solid immersion lens, there can be an additional mode of operation when evanescent waves are generated to explore surface plasmon resonance effect to further enhance defect detection.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. For example, the defect detection characteristic data may be obtained from a transmitted, reflected, or a combination output beam. Accordingly, the present embodiments are to be considered as illustrative and not restrictive, and the invention is not to be limited to the details given herein.

What is claimed is:

1. A system for detecting defects in a semiconductor sample, the system comprising:
    an illumination optics module for simultaneously scanning two or more structured illumination (SI) patterns across the sample in a scan direction, wherein the two or more SI patterns have a phase shift with respect to each other and wherein the two or more SI patterns are arranged in sequence along the scan direction;
    a collection optics module for collecting output light from the sample in response to the SI patterns that are scanned across the sample;
    two or more detectors for individually detecting the output light collected for individual ones of the SI patterns; and
    a controller operable to perform the following operations:
        generating two or more SI images for the two or more SI patterns based on the individually detected output light; and
        detecting defects on the sample by performing a comparison type inspection process based on the two or more SI images.

2. The system of claim 1, wherein the illumination optics module are configured for simultaneously scanning three structured illumination (SI) patterns across the sample in the scan direction, wherein the phase shift between the three SI patterns is ⅓ a cycle of the SI patterns.

3. The system of claim 1, wherein the number of SI patterns is selected so as to optimize defect detection coverage by the SI patterns.

4. The system of claim 1, wherein the controller is further configured to cause the illumination optics module and the collection optics module to operate in a dark field inspection mode.

5. The system of claim 1, wherein the illumination optics module is configured to generate the SI patterns on the sample by directing two sets of illumination beams from two opposite directions onto the sample, wherein the illumination beams of each of the two sets are phase shifted with respect to each other, wherein the two sets of illumination beams interfere with each other to produce the two or more SI patterns on the sample.

6. The system of claim 1, wherein the phase offset of the two or more SI patterns is fixed.

7. The system of claim 1, wherein the illumination optics module comprises:
    a coherent light source for generating an illumination beam;
    a first beam splitter for receiving the illumination beam and outputting the two or more illumination beams;
    a first collimator for receiving the two or more illumination beams from the splitter and bringing the two or more illumination beams into a parallel propagation;

a phase-shifting splitter for receiving the two or more illumination beams from the first collimator and outputting a pair of split illumination beams for each of the two or more illumination beams, wherein the pairs of split illumination beams are phase offset relative to one another;

a second collimator for receiving the two or more pairs of split illumination beams; and illumination optics for directing towards the sample a first set of illumination beams that include a first one of each pair of split illumination beams and a second set of illumination beams that include a second other one of each pair of split illumination beams so as to form the two or more SI patterns on the sample.

8. The system of claim 7, wherein the phase-shifting splitter is a diffractive optical element (DOE) and includes two or more beam splitting grating sections for the two or more illumination beams that are received by the DOE, wherein the two or more beam splitting grating sections have a phase offset relative to each other so as to cause the phase offset of the two or more SI patterns.

9. The system of claim 1, wherein the illumination optics module comprises:

a coherent light source for generating an illumination beam;

a first beam splitter for receiving the illumination beam and outputting the two or more illumination beams;

a first collimator for receiving the two or more illumination beams from the splitter and bringing the two or more illumination beams into a parallel propagation;

a splitter for receiving the two or more illumination beams from the first collimator and outputting a pair of split illumination beams for each of the two or more illumination beams;

a second collimator for receiving the two or more pairs of split illumination beams; and illumination optics for directing towards the sample a first set of illumination beams that include a first one of each pair of split illumination beams and a second set of illumination beams that include a second other one of each pair of split illumination beams, and wherein the illumination optics include a first phase-shifting element for receiving the first set of illumination beams and a second phase-shifting element for receiving the second set of illumination beams, wherein the first and second phase-shifting elements are configured to cause the first and second sets of illumination beams to be phase offset relative to one another so as to induce the phase shift for the two or more SI patterns on the sample.

10. The system of claim 1, wherein the two or more SI patterns are spatially separate while being simultaneously scanned across the sample so as to be scanned over two or more spatially separate portions of the sample.

11. The system of claim 1, wherein the illumination optics module is configured to direct two sets of phase-shifted illumination beams from diagonal directions towards the sample to form the two or more SI patterns on the sample, the system further comprising one or more rectangular apertures positioned at the pupil plane of the collection optics to suppress pattern noise.

12. The system of claim 1, wherein the collection optics module further comprises one or more optical pupil filters to reduce noise due to ringing of imaging point spread function.

13. The system of claim 11, wherein the collection optics module further comprises a linear polarizer so as to modulate by a phase shift a signal detected by each detector.

14. The system of claim 1, wherein the illumination optics module includes an immersion lens through which two sets of phase-shifted illumination beams are directed from opposite directions onto the sample so as to form the two or more SI patterns.

15. The system of claim 1, wherein the illumination optics module is configured to generate the SI patterns on the sample by directing two sets of illumination beams from orthogonal angles.

16. A method for inspecting a semiconductor sample, comprising:

simultaneously directing two or more structured illumination (SI) fringe patterns that are phase-shifted with respect to each other onto a sample;

scanning the two or more SI fringe patterns relative to the sample so that the two or more SI fringe patterns are aligned parallel to a scan direction;

detecting spatially separated two or more output signals that each corresponds to an individual one of the two or more SI fringe patterns;

generating an image from each of the two or more output signals;

comparing each generated image to a corresponding reference image to obtain one or more difference values and generate a defect image that includes one or more detected defects that each correspond to a difference value that is above a predetermined threshold; and merging the defect images from the two or more output signals.

17. The method of claim 16, wherein comparing is accomplished by a die-to-die or cell-to-cell inspection process that includes defining a difference between each image and its corresponding reference image as a defect when the difference exceeds a predetermined threshold.

18. The method of claim 16, wherein two or more different thresholds are used for the two or more SI images.

19. The method of claim 16, further comprising subtracting a known fringe profile from each output signal so as to obtain a real defect signal.

20. The method of claim 16, wherein the two or more SI fringe patterns are spatially separate while being simultaneously scanned across the sample so as to be scanned over two or more spatially separate portions of the sample.

21. The method of claim 16, wherein the phase offset of the two or more SI patterns is fixed.

* * * * *